United States Patent [19]

Callewaert

[11] Patent Number: 5,726,170
[45] Date of Patent: Mar. 10, 1998

[54] CLAVULANIC ACID SALTS

[75] Inventor: George Leo Callewaert, Penn, United Kingdom

[73] Assignee: Spurcourt Limited, Woodley Reading, United Kingdom

[21] Appl. No.: 605,367

[22] Filed: Feb. 22, 1996

[30] Foreign Application Priority Data

Feb. 25, 1995 [GB] United Kingdom ............ 9503839
Oct. 12, 1995 [GB] United Kingdom ............ 9520915

[51] Int. Cl.$^6$ .................. C07D 503/00; A61K 31/395; A61K 31/43; A61K 31/545
[52] U.S. Cl. ............ 514/210; 514/195; 514/202; 514/208; 540/349
[58] Field of Search ............... 540/349; 514/210, 514/195, 202, 208

[56] References Cited

FOREIGN PATENT DOCUMENTS

| 862211 | 6/1978 | Belgium . |
| 0026044 | 4/1981 | European Pat. Off. . |
| 0387178 | 9/1990 | European Pat. Off. . |
| 0182522 | 6/1991 | European Pat. Off. . |
| 2733230 | 8/1993 | Germany . |
| 1508977 | 4/1978 | United Kingdom . |
| 1543563 | 4/1979 | United Kingdom . |
| 157873 | 9/1980 | United Kingdom . |
| 2287025 | 4/1995 | United Kingdom . |
| 2287026 | 4/1995 | United Kingdom . |
| 2264944 | 9/1995 | United Kingdom . |
| 9325557 | 12/1993 | WIPO . |
| 9422873 | 10/1994 | WIPO . |

*Primary Examiner*—Mukund J. Shah
*Assistant Examiner*—King Lit Wong
*Attorney, Agent, or Firm*—Kohn & Associates

[57] ABSTRACT

The salts are prepared by reacting a benzhydrylamine of the formula I (or a salt thereof) with clavulanic acid (or a salt thereof) in solvent, and isolating the resulting salt. In formula I, each of $R^1$ and $R^2$ is hydrogen (preferred) or an acceptable substituent.

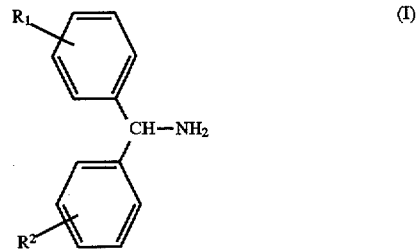

The clavulanic acid salts can be used in pharmaceutical formulations together with a pharmaceutically acceptable carrier, and, preferably, a beta-lactam antibiotic.

19 Claims, 2 Drawing Sheets

CLAVULANIC ACID SALTS

The present invention relates to clavulanic acid salts, the preparation thereof, and pharmaceutical compositions containing such salts.

BACKGROUND OF THE INVENTION

Clavulanic acid is known to be active in antibiotic formulations, because it inhibits many of the beta-lactamase enzymes which cleave the beta-lactam ring of anti-microbial agents such as penicillins and cephalosporins. Clavulanic acid, therefore, improves the antibacterial actions of such anti-microbial agents. Clavulanic acid has the following formula:

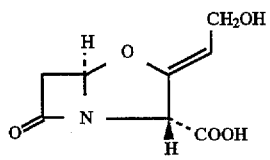

British patent 1578739 discloses a class of amine salts of clavulanic acid, and a process for the preparation of clavulanic acid salts, which may be more easily formulated than previously described salts of clavulanic acid to stable pharmaceutical compositions. Typically, amine salts of clavulanic acid either do not crystallize, or only crystallize on addition of very large amounts of solvent, such as acetone.

PCT patent specification 93/25557 discloses a broad range of amines for use as intermediates in the preparation of clavulanic acid or pharmaceutically acceptable salts and esters.

Clavulanic acid is typically recovered from aqueous solution by acidification and extraction into an organic solvent. It is therefore highly advantageous to be able to crystallize a clavulanic acid salt direct from this solvent extract without the addition of other solvents.

Only a few primary amines have been reported as being able to cause crystallization of clavulanic acid as the amine salt direct from a single water immiscible organic solvent such as ethyl acetate. An example of such a primary amine is tertiary octylamine (which is disclosed in British patent 2264944), which gives a purified white crystalline amine salt of clavulanic acid, provided that the solution of clavulanic acid in the solvent does not contain too high a level of impurities. These primary amines are all of the aliphatic type.

SUMMARY OF THE INVENTION

I have, surprisingly, found that a specific category of aromatic organic amines, namely certain benzhydrylamines, which have not been previously disclosed, confer significant advantages in preparing a clavulanic acid salt from an organic solvent used in extracting clavulanic acid.

I have found that benzhydrylamine and related compounds, despite being aromatic organic substances which might normally be expected to associate with organic impurities will cause clavulanic acid to crystallize as a purified white amine salt direct from an organic solvent, such as ethyl acetate.

Accordingly, there is provided by a first aspect of the present invention, a clavulanic salt derived from clavulanic acid (or a salt thereof) and a benzhydrylamine of the formula I (or a salt thereof),

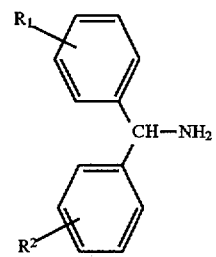

wherein each of $R^1$ and $R^2$ independently represents a hydrogen atom or a pharmaceutically acceptable substituent, such as a lower alkyl, haloalkyl, alkoxyl or acyloxy group or the like.

Advantageously, such an amine of formula I forms highly pure salts with clavulanic acid, which salts have exceptionally beneficial color and chemical stability characteristics, and also relatively low solubility in water. In using a solvent, such as ethyl acetate, for isolation of the clavulanic salts according to the invention, there is in many cases no necessity for any addition of a second solvent, such as acetone. If, however, the organic solvent extract contains a significant level of impurities, it is desirable to increase the polarity of the crystallization medium prior to addition of the amine. This is most conveniently achieved by the addition of a second more polar solvent such as a ketone or an alcohol. It has accordingly been found that, as with other amines, when necessary, the purity and general quality of the benzhydrylamine salt of clavulanic acid may be enhanced by the addition of a suitable secondary solvent to the ethyl acetate extract. Acetone is a preferred secondary solvent.

The clavulanic salts according to the invention are themselves pharmaceutically acceptable, and may therefore be used, together with a carrier, diluent or excipient, in a pharmaceutical formulation. Alternatively, the clavulanic salts may be used as intermediates for the preparation of further pharmaceutically acceptable salts of clavulanic acid, such as the potassium salt; such further salts may themselves be used according to the invention in a pharmaceutical formulation.

A pharmaceutical formulation according to the invention preferably also contains a beta-lactam antibiotic, more preferably a penicillin or a cephalosporin. Alternatively, a pharmaceutical formulation according to the invention may be co-administered with such a beta-lactam antibiotic. Thus the effectiveness of such a beta-lactam antibiotic can be maintained or improved when administered with a pharmaceutically acceptable salt in a pharmaceutical formulation according to the invention.

According to another aspect of the present invention, there is provided a process for preparing a salt of clavulanic acid (as defined above), which comprises reacting a benzhydrylamine of the above formula (I) or a salt thereof, with clavulanic acid (or a salt thereof) in an organic solvent, and isolating the resulting salt. Preferably the solvent comprises an aliphatic carboxylic ester or an aliphatic ketone; a preferred such solvent is ethyl acetate.

Where the clavulanic salt isolated contains a significant level of impurities, the process preferably further comprises addition of a second more polar solvent such as an alcohol or a ketone (preferably acetone).

The clavulanic salts according to the invention have been found to be non-hygroscopic and may even be recovered direct from aqueous solution. This may be achieved either by evaporation of water from an aqueous solution of the clavulanic salts or by preparing the clavulanic salt in aqueous solution under conditions of high clavulanate ion concentration. This is a unique property of the instant clavulanic salts, because no other amine salts are known to be recoverable from aqueous solution in this way.

According to a further aspect of the present invention, there is provided a process for preparing a salt of clavulanic acid according to the first aspect of the present invention, which process comprises reacting an aqueous solution of clavulanic acid (or a salt thereof) having a pH in the range of 6 to 8 and a clavulanate concentration of at least 5% by weight, with an equivalent amount of a water soluble salt (such as a hydrochloride salt) of a benzhydrylamine of formula I, stirring the mixture for several hours at a temperature of 0° to 5° C., such that the clavulanic acid salt precipitates from the solution, and can be filtered off.

Alternatively, the clavulanic salt may be isolate from an aqueous solution of the clavulanic salt by concentration under conditions of reduced pressure and at a temperature not exceeding 25° C., such that after stirring the mixture for several hours at a temperature from 0°–5° C., the clavulanic salt precipitates from the mixture, and can be filtered off.

These processes for preparing the clavulanic acid salts according to this aspect of the present invention have the significant advantage that no organic solvent is required in order to recover the salts.

According to a yet further aspect of the present invention there is provided a process for preparing a benzhydrylamine salt of clavulanic acid having a novel crystal habit, which process comprises preparing a substantially water free solution of clavulanic acid (or a salt thereof) in an organic solvent, such as ethyl acetate, which solution is kept at a temperature of between approximately 0° and 15° C. (preferably less than 10° C.) and reacting with a benzhydrylamine of formula I in the organic solvent. The process advantageously causes a benzhydrylamine salt of clavulanic acid to crystallize substantially in the form of small spherical crystals. This is a yet further unique property of the clavulanic salts according to the invention because all other amine salts of clavulanic acid for which data have been reported crystallize mostly as needles or occasionally as prisms or platelets. The new spherical crystal form is highly advantageous because the crystallization mixture has a low viscosity and the crystal bulk density associated with the salt is higher, thus allowing crystallization of more concentrated mixtures. The clavulanic salt is also easier to filter and wash and, when dried, the resulting powder-like product has superior flow and handling characteristics.

As is well known from the scientific literature, certain amine salts of clavulanic acid have been shown to form hydrates and solvates. Generally such compounds are not well defined and are of variable composition. Also, on some occasions, in order to demonstrate their existence, it has been necessary to contrive conditions which would not ordinarily apply during a process to recover and purify clavulanic acid. In any case, the formation of solvates can be a considerable nuisance because of the inevitable carry over of solvent to subsequent processing stages. The benzhydrylamine salts of clavulanic acid according to the invention do not normally form solvates with the solvents commonly used in clavulanic acid extraction and purification processes. However, their existence as transient or low level intermediates in which the solvent is loosely bound cannot be totally discounted. Therefore the salts of clavulanic acid and benzhydrylamine of formula I, in which there are present some small amounts of solvent or water, are to be considered as falling within the scope of the present invention.

DETAILED EXAMPLES

Figure 1:
FIG. 1 is a photomicrograph of crystals of the benzhydrylamine salt of clavulanic acid.

Exemplary processes for the preparation of benzhydrylamine salts of clavulanic acid will now be described in the following detailed Examples.

Example 1

Preparation of the Benzhydrylamine Salt of Clavulanic Acid

A magnesium sulfate and decolorising charcoal treated solution of clavulanic acid (3.0% w/v clavulanic acid) in ethyl acetate was prepared conventionally. To 100 ml of this solution was slowly added, with stirring, a solution of 4.15 grams of benzhydrylamine (approximately 20% w/v solution in ethyl acetate). After about 20% of the amine had been added, a few milligrams of benzhydrylamine clavulanate was added as a crystallization seed. Addition of the remainder of the benzhydrylamine caused the desired salt to crystallize.

Crystallization of the mixture was completed by stirring at ambient temperature for 30 minutes and then at 0°–3° C. for a further two hours. The white crystalline product, in the form of needle shaped crystals, was then filtered, washed with a little ethyl acetate and dried in vacuo to yield 4.6 grams of salt (yield 80%). The benzhydrylamine salt of clavulanic acid was subjected to elemental analysis, the results of which are as follows:

| | | |
|---|---|---|
| Carbon (% m/m) | 66.36 | (calculated 65.96) |
| Hydrogen (% m/m) | 5.80 | (calculated 5.80) |
| Nitrogen (% m/m) | 7.29 | (calculated 7.32) |
| Melting point (°C.) | 134–135 | |

Figure 3:
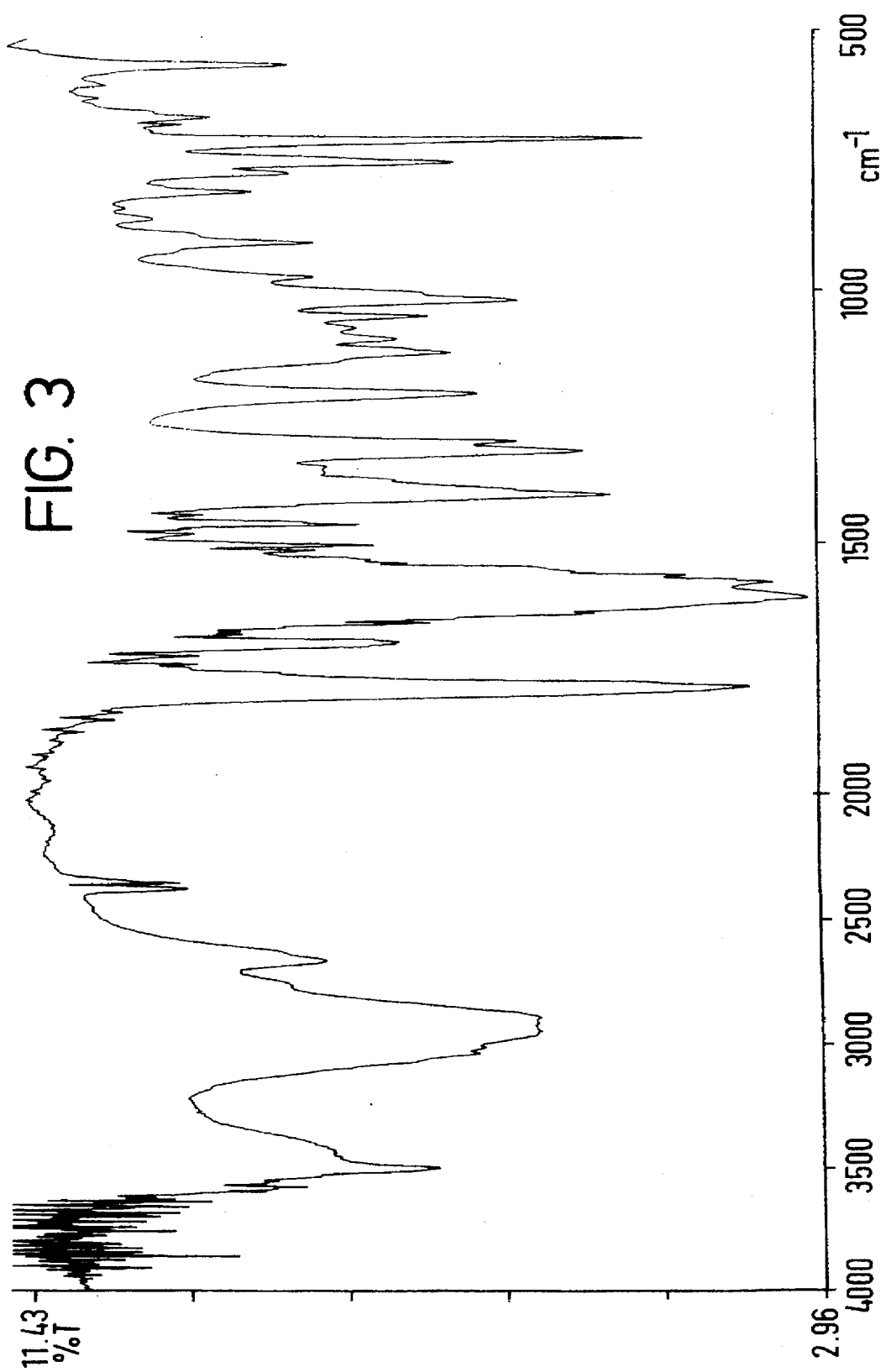
FIG. 3 is an infra-red spectrum of the benzhydrylamine salt of clavulanic acid.

The shape of the crystals obtained is shown in the photomicrograph of FIG. 1 and the infra-red spectrum of the salt is shown in FIG. 3.

EXAMPLE 2

Preparation of the Benzhydrylamine Salt of Clavulanic Acid in the Form of Spherical Crystals.

A decolorising charcoal treated solution of clavulanic acid (0.25% w/v clavulanic acid) in ethyl acetate was prepared conventionally. One liter of this solution was reduced in volume to 100 ml under reduced pressure on a rotary evaporator. To this solution at 10° C. was added rapidly, with stirring, a solution of 3.5 grams of benzhydrylamine (approximately 20% w/v solution in ethyl acetate). Crystallization was completed by stirring at 10° C. for 30 minutes and then at 0°–3° C. for a further two hours. The white crystalline product in the form of small, rapidly settling, crystal spheres was then filtered, washed with a little ethyl acetate and dried in vacuo to yield 4.1 grams of salt (yield 85%). The benzhydrylamine salt of clavulanic acid in the form of spherical crystals was subjected to elemental analysis, the results of which are as follows:

| | | |
|---|---|---|
| Carbon (% m/m) | 65.73 | (calculated 65.96) |
| Hydrogen (% m/m) | 5.83 | (calculated 5.80) |
| Nitrogen (% m/m) | 6.96 | (calculated 7.32) |

Figure 2:
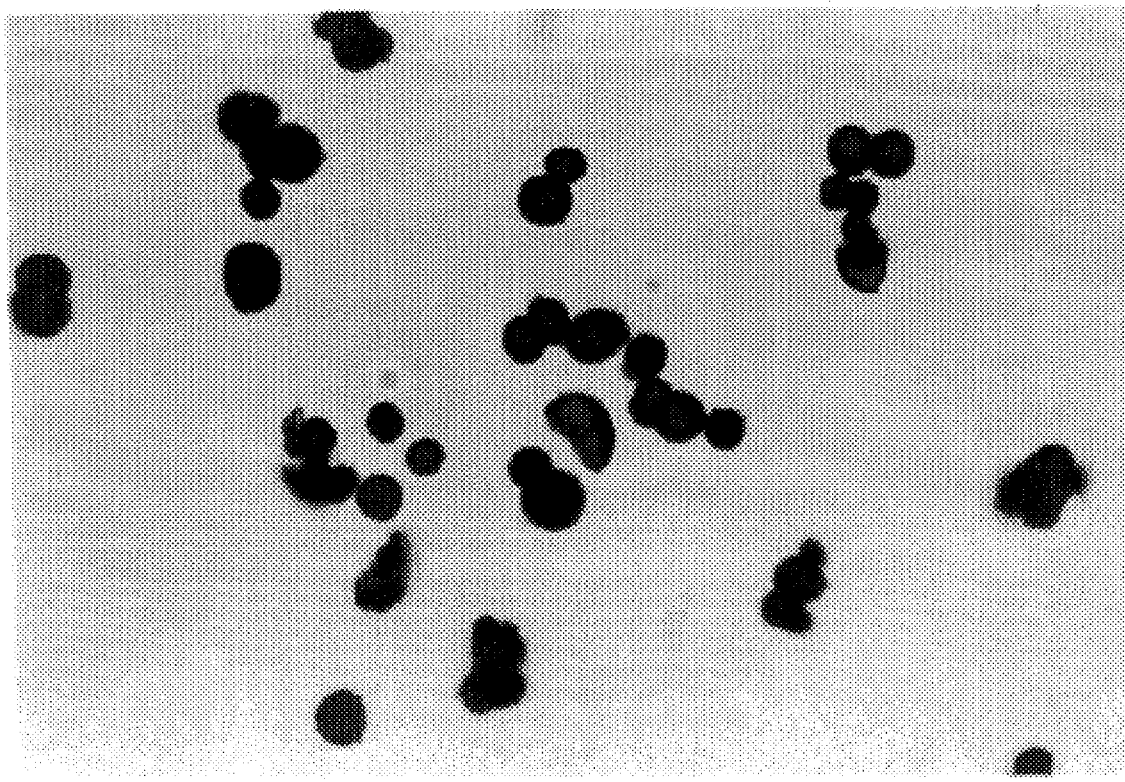
FIG. 2 is a photomicrograph of spherical crystals of the benzhydrylamine salt of clavulanic acid.

The shape of the crystals obtained is shown in the photomicrograph of FIG. 2.

EXAMPLE 3

Preparation of the Potassium Salt of Clavulanic Acid

With stirring at ambient temperature, 3.8 grams of the benzhydrylamine salt of clavulanic acid were dissolved in 100 ml. butan-1-ol which contained 2.0% v/v water. To this solution was added 7.0 ml of a 2N solution of potassium 2-ethyl hexanoate in butan-1-ol with continued stirring. After completion of this addition, the mixture was stirred at ambient temperature for one hour and then at 0°–3° C. for a further hour. The product, which was in the form of a thick crystal slurry was filtered, washed with butan-1-ol and then acetone and dried in vacuo to yield 1.9 grams of the salt (yield 80.6%).

EXAMPLE 4

Crystallization of benzhydrylamine salt of clavulanic acid in acetone/ethyl acetate and conversion to potassium clavulanate (a) 11.0 grams (3 equivalents) of benzhydrylamine was added dropwise with stirring to 190 ml of a mixture of ethyl acetate/acetone (1:1 v/v) containing 19.7 grams/ liter of clavulanic acid. After addition of about 6 ml of the benzhydrylamine, crystallization commenced. After completing the addition the mixture was stirred for about one hour. The crystalline product was filtered off under suction, washed with cold acetone and dried in vacuo. The yield of the benzhydrylamine salt of clavulanic acid was 5.30 grams (73.7%) with a clavulanic acid content of 51.9% (theoretically 52%).

(b) To 3.6 grams of the benzhydrylamine salt of clavulanic acid was added 1.2 equivalents of potassium 2-ethyl hexanoate. The yield of potassium clavulanate was 2.17 grams (99%) as white crystals with a clavulanic acid content of 85.7% (theoretically 83.6%).

EXAMPLE 5

Crystallization of benzhydrylamine salt of clavulanic acid in ethyl acetate and conversion to potassium clavulanate.

(a) 9.2 grams (3 equivalents) of benzhydrylamine was added dropwise at 5° C. with stirring to 90 ml ethyl acetate containing 36.4 grams/liter clavulanic acid. After stirring for half an hour, the crystalline product was filtered off under suction, washed with ethyl acetate and dried in vacuo. The yield of the benzhydrylamine salt of clavulanic acid was 6.62 grams (97.7%), as light yellow crystals with a clavulanic acid content of 48.7%.

(b) 4.8 grams of the benzhydrylamine salt of clavulanic acid was converted into potassium clavulanate as described in Example 4. The yield of potassium clavulanate was 2.59 grams (94%) as almost white crystals with a clavulanic acid content of 83.8%.

EXAMPLE 6

Recovery of the Benzhydrylamine Salt of Clavulanic Acid from Water

With stirring at ambient temperature, 1.0 gram of the benzhydrylamine salt of clavulanic acid was dissolved in 15 ml. water. A small amount of insoluble material was filtered off. The resulting solution was then concentrated by evaporation using a rotary evaporator with a bath temperature of 25° C. to a volume of ca. 5 ml. This solution was then gently stirred overnight at a temperature of 0°–3° C., during which time the benzhydrylamine salt of clavulanic acid precipitated.

In further experiments, similar solutions of salts of clavulanic acid with other amines, in which the clavulanic acid solution content was ca. 3.5% w/v, were prepared and subjected to the same conditions.

These other amines included tertiary-butylamine, cyclohexylamine, dimethylethylamine, 2-methyl-2-amino-1-propanol and dimethylbenzylamine. None of these amine salts of clavulanic acid could be precipitated under the conditions described.

What we claim is:

1. A salt of clavulanic acid and a benzhydrylamine of the formula I

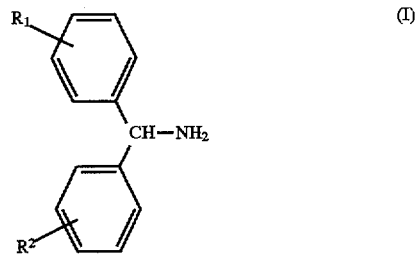

wherein each of $R^1$ and $R^2$ independently represents a hydrogen atom or a radical selected from the group consisting of lower alkyl, haloalkyl, acyloxy and alkoxy.

2. A salt according to claim 1, in the form of substantially spherical crystals.

3. A salt according to claim 1, wherein $R^1$ and $R^2$ are both hydrogen.

4. A process for preparing a salt of clavulanic acid according to claim 1, which comprises reacting a benzhydrylamine of the formula I according to claim 1, or a salt thereof, with clavulanic acid, or a salt thereof, in an organic solvent, and isolating the resulting salt.

5. A process according to claim 4, wherein said organic solvent comprises an aliphatic carboxylic ester or an aliphatic ketone.

6. A process according to claim 5, wherein said organic solvent is ethyl acetate.

7. A process according to claim 5, wherein said organic solvent comprises a polar solvent and a relatively less polar solvent.

8. A process according to claim 7, wherein said polar solvent is acetone.

9. A process for the preparation of clavulanic acid, which comprises converting a salt according to claim 1 into clavulanic acid.

10. A process for preparing a salt of clavulanic acid according to claim 1, which comprises reacting an aqueous solution of a salt of clavulanic acid, the solution having a pH in the range of about 6 to 8 and a clavulanic acid concentration of at least 5% by weight, with an equivalent amount of a water soluble salt of a benzhydrylamine of the formula (I) according to claim 1, and isolating the resulting salt by stirring the mixture at a temperature of from 0° to 5° C., and filtering the resulting precipitated salt from the solution.

11. A process according to claim 10, wherein the water soluble salt of said benzhydrylamine is the hydrochloride salt.

12. A process for isolating a salt of clavulanic acid according to claim 1, which comprises concentrating an aqueous solution of the salt of clavulanic acid according to claim 1 under conditions of reduced pressure and at a temperature not exceeding 25° C., stirring the mixture for several hours at 0°–5° C. and filtering the clavulanic salt from the solution.

13. A process for preparing a salt of clavulanic acid according to claim 1, in the form of substantially spherical crystals, which process comprises preparing a substantially water free solution of clavulanic acid in an organic solvent at from approximately 0° to 15° C. and reacting a benzhydrylamine of the formula (I) according to claim 1 (or a salt thereof) with said clavulanic acid in said solution, and isolating the resulting salt.

14. A process according to claim 13, wherein said organic solvent comprises ethyl acetate.

15. A process according to claim 13, wherein said water free solution of clavulanic acid in an organic solvent is prepared at less than 10° C.

16. A pharmaceutical formulation, which comprises a salt of clavulanic acid according to claim 1, or a pharmaceutically acceptable salt of clavulanic acid prepared by a process according to claim 4; together with a pharmaceutically acceptable carrier, diluent or excipient therefor.

17. A pharmaceutical formulation according to claim 16, which also contains a beta-lactam antibiotic.

18. A pharmaceutical formulation according to claim 17, wherein said antibiotic is selected from the group consisting of a penicillin and a cephalosporin.

19. A method of improving the antibacterial action of a beta-lactam antibiotic, which comprises administering said antibiotic to a patient together with a salt of clavulanic acid according to claim 1.

* * * * *